(12) United States Patent
Song et al.

(10) Patent No.: US 9,566,079 B2
(45) Date of Patent: Feb. 14, 2017

(54) SINGLE PROBE WITH DISTURBER

(71) Applicant: Cybersonics, Inc., Erie, PA (US)

(72) Inventors: Tao Song, Erie, PA (US); Shu Du, Erie, PA (US); Yuan Song, Shenzhen (CN)

(73) Assignee: Cybersonics, Inc., Erie, PA (US)

( * ) Notice: Subject to any disclaimer, the term of this patent is extended or adjusted under 35 U.S.C. 154(b) by 0 days.

(21) Appl. No.: 14/933,234

(22) Filed: Nov. 5, 2015

(65) Prior Publication Data
US 2016/0051269 A1 Feb. 25, 2016

Related U.S. Application Data

(63) Continuation of application No. 12/657,248, filed on Jan. 15, 2010, now Pat. No. 9,254,140.

(30) Foreign Application Priority Data

Apr. 27, 2009 (CN) .......................... 2009 1 0136077

(51) Int. Cl.
*A61B 17/22* (2006.01)
*A61B 17/3207* (2006.01)

(52) U.S. Cl.
CPC ..... *A61B 17/22012* (2013.01); *A61B 17/3207* (2013.01)

(58) Field of Classification Search
CPC ...................... A61B 17/22012; A61B 17/3207; A61B 17/22004; H04B 3/56
See application file for complete search history.

(56) References Cited

U.S. PATENT DOCUMENTS 4,311,145 A * 1/1982 Esty .................... A61B 18/1482
606/42
4,979,952 A * 12/1990 Kubota ............ A61B 17/22012
310/316.01

(Continued)

FOREIGN PATENT DOCUMENTS

EP 0353294 B1 8/2000
EP 0722296 B1 4/2003

*Primary Examiner* — Julie A Szpira
(74) *Attorney, Agent, or Firm* — Ulmer & Berne LLP

(57) ABSTRACT

A single probe percutaneous surgical instrument for de-bulking/removing thrombus/clog/calculi has an actuator assembly (4), a probe set (13), an operating switch (10), and a generator (12). The actuator assembly (4) has a proximal end (4a) and a distal end (4b), a cable connector (1), a suction connector (2), and actuator switch (3) mounted with the proximal end (4a) and a horn (5) mounted at the distal end (4b). The probe set (13) is mounted to the horn (5) and includes at least one disturber (6), a spring (7), a 10 spring adjusting nut (8) and a fixed probe (9), the cable connector (1) connecting to the generator (12) through a cable, and the suction connector (2) connecting to a suction system. The actuator switch (3) controls a probe vibration mode through the generator (12), the actuator assembly (4) comprising at least two piezoelectric ceramic rings (18) assembled with a bolt (15), the horn (5) and a back plated (16). The horn (5) is mounted on the distal end (4b) of the actuator assembly (4), the horn (5) being coupled with the bolt (15) and the piezoelectric rings (18), the at least one disturber (6) and the spring (7) being mounted on the fixed probe (9) using the spring adjusting nut (8). The generator (12) includes a microprocessor and the microprocessor is programmed to control the actuator vibration mode, the fixed probe optimal vibration frequency and the disturbing strength of the disturbers.

6 Claims, 2 Drawing Sheets

(56) References Cited

U.S. PATENT DOCUMENTS

| | | | |
|---|---|---|---|
| 5,879,314 A | 3/1999 | Peterson et al. | |
| 6,558,397 B2* | 5/2003 | Hirt | A61B 17/22012 606/127 |
| 6,875,220 B2* | 4/2005 | Du | A61B 17/22012 604/22 |
| 6,942,677 B2* | 9/2005 | Nita | A61B 17/22012 604/22 |
| 7,387,612 B2 | 6/2008 | Pal et al. | |
| 2002/0010478 A1* | 1/2002 | Menne | A61B 17/22012 606/128 |
| 2002/0010486 A1* | 1/2002 | Hirt | A61B 17/22012 606/169 |
| 2004/0010267 A1* | 1/2004 | Nakamura | A61B 17/22012 606/128 |
| 2005/0209620 A1 | 9/2005 | Du et al. | |
| 2007/0066978 A1* | 3/2007 | Schafer | A61B 5/02007 606/128 |
| 2007/0162050 A1* | 7/2007 | Sartor | A61B 17/32006 606/128 |
| 2008/0061784 A1 | 3/2008 | Pal et al. | |

* cited by examiner

SINGLE PROBE WITH DISTURBER

CROSS REFERENCE TO RELATED APPLICATIONS

This application is a continuation of U.S. patent application Ser. No. 12/657,248 filed on Jan. 15, 2010, which claims priority from Chinese Patent Application No. 200910136077.0, filed on Apr. 27, 2009.

BACKGROUND OF THE INVENTION

Field of the Invention The present invention is generally directed to a surgical instrument for disintegrating/removing thrombus, clog and calculi. It is more particularly directed to percutaneous surgical instruments for use in cardiac, blood vessel surgical application and endoscopic procedures.

Description of Related Art

Fixed ultrasonic probe devices that operate in the frequencies 20-30 kHz range are best in disintegrating thrombus and clog using cavitations. It is known that sweeping around resonant frequency introduces a disturbance which gives even better performance for disintegration. This invention will have additional low frequency mechanical disturbance.

SUMMARY OF THE INVENTION

It is the object of the invention to enhance the application of ultrasound in the treatment of thrombi and clogs or clots.

It is another object of the invention to improve ultrasound treatment of thrombi and other obstructions.

These objects are accomplished, in one aspect of the invention, by the provision of a single, fixed probe that utilizes vibration disturbers. In another aspect of the invention, the object are accomplished by the provision of a percutaneous surgical instrument for de-bulking/removing thrombus/clog/calculi comprising: an actuator assembly, a probe set, an operating switch, and a generator, the actuator assembly having a proximal end and a distal end, a cable connector, a suction connector, and actuator switch mounted with the proximal end and a horn mounted at the distal end; the probe set being mounted to the horn and including at least one disturber, a spring, a spring adjusting nut and a fixed probe, the cable connector connecting to the generator through a cable, the suction connecting to a suction system; the actuator switch controlling a probe vibration mode through the generator, the actuator assembly comprising: at least two piezoelectric ceramic rings assembled with a bolt, the horn and a back plate; the horn being mounted on 10 the distal end of the actuator assembly, the horn being coupled with the bolt and the piezoelectric rings, the at least one disturber and the spring being mounted on the fixed probe using the spring adjusting nut, the generator including a microprocessor and the microprocessor being programmed to control the actuator vibration mode, the fixed probe optimal vibration frequency and the disturbing strength of the disturbers.

The use and application of the disturbers increases the efficacy of instrument. Further, the use of the vibrational disturbers allows a single probe to be used for small work channel scope operations in cardiac and blood vessel surgical 20 applications as well as other endoscopy procedures.

BRIEF DESCRIPTION OF THE DRAWING(S)

DESCRIPTION OF THE INVENTION

Figure 1:
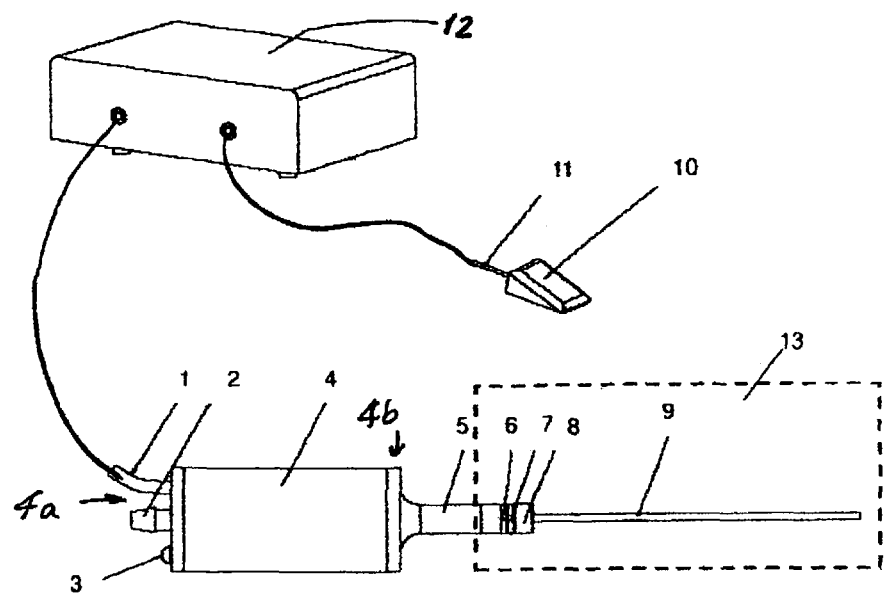
FIG. 1 is a diagrammatic view, in perspective, of an aspect of the invention.
Figure 2:
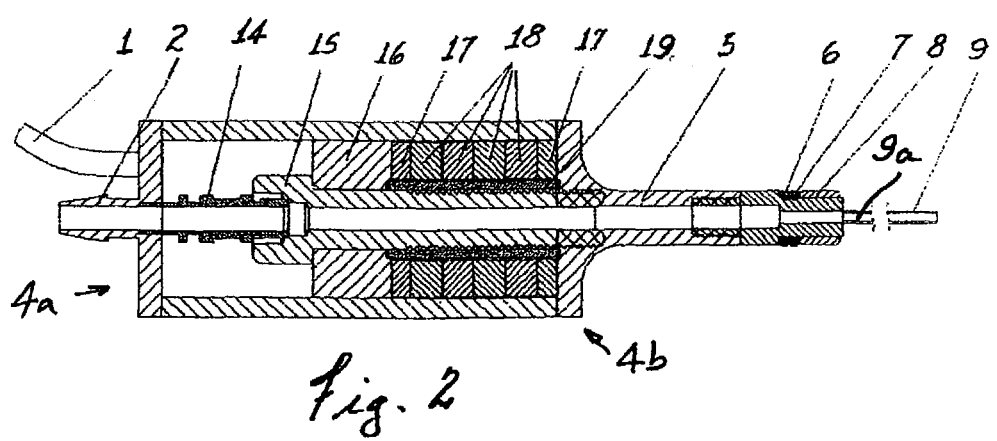
FIG. 2 is an elevation, sectional view of an actuator in accordance with an aspect of the invention.
Figure 3:
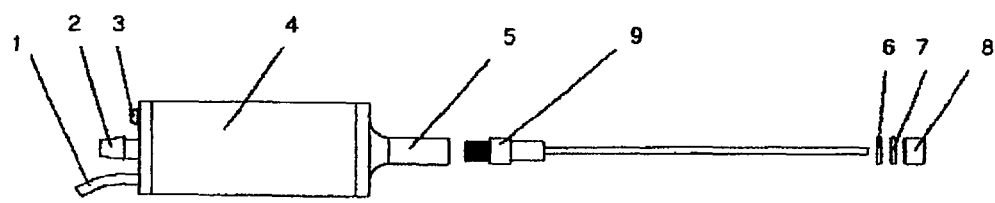
FIG. 3 is an exploded view of an embodiment of the invention.
Figure 4:
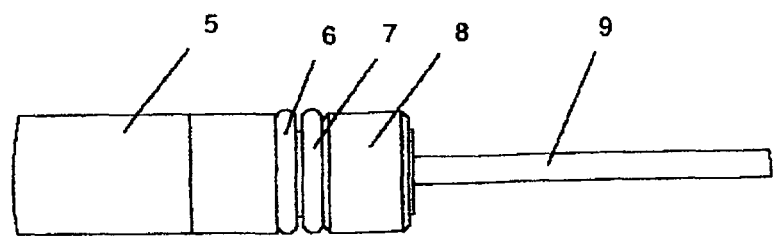
FIG. 4 is an enlarged view of the distal end of the instrument illustrating a disturber in a position to move to contact a second disturber or spring.

For a better understanding of the present invention, together with other and further objects, advantages and capabilities thereof, reference is made to the following disclosure and appended claims taken in conjunction with the above-described Referring now to the drawings with greater particularity, there is shown in FIG. 1 a percutaneous surgical instrument for disintegrating/removing thrombus, clog and 10 calculi. The instrument includes generally an actuator 4, a probe set 13, a switch for controlling the operation, which can be a footswitch 10 and a power supply such as a generator 12.

The actuator 4 has a cable connector 1 that connects to the generator 12, a suction 15 connector 2, which can connect to a supply of suction, not shown, an actuator switch 3 preferably attached to the proximal end 4a of the actuator 4 and the horn.

The actuator body 4 comprises at least 2 piezoelectric crystals 18, that can be ceramic rings, that are assembled with the bolt 15, the horn 5 and the back plate 16. The bolt 15 applies pre-stress on the piezoelectric ceramic crystal rings 18. The function of the actuator 4 is to transfer the electric energy from the generator 12 to the mechanical vibration energy.

The horn 5 is positioned on the distal end 4b of the actuator 4 and is coupled with the bolt 15 and the piezoelectric rings 18 to amplify the vibration of the rings 18. The disturbers 6 are mounted on the horn 5 and contribute additional vibration frequency. The amplitude and frequency of this additional vibration is dependent on the movement of the disturbers where the movement is controlled by the adjusting nut position. Introducing disturbance to such a system can generate a desired overshoot if it can be controlled properly. This property of controlled overshoot can generate strong impulses from the force to the probe. A controlled driving signal from the generator, in combination with the nut position between the disturbers, adjusts the impact to the thrombus, clog and calculi thru the probe.

The disturber 6, which can be more than one, and including the spring 7, are mounted on the probe 9 for disturbing the ultrasonic vibration to increase the de-bulking rate or removing rate. The adjusting nut 8 is used for changing the disturbing frequencies in accordance with the nut position on the probe.

In a preferred embodiment of the invention, the disturbers are stainless steel rings 10 and there at least two of them.

The fixed probe 9 can include a lumen 9a when suction is applicable, or it can be a simple, solid wire in those cases in which suction is not necessary.

Generally, the disturbers are driven by the generator 12 through the actuator 4 and the fixed probe 9 with various frequencies, pulse cycle frequencies and duty cycles to maximize the efficiency of the thrombi break-up.

The size of the disturbers may be varied in use for different driven frequencies and maximizing the disturbing frequencies to breakup and/or remove the thrombi/clog/calculi.

While there have been shown and described what are at present considered to be the preferred embodiments of the invention, it will be apparent to those skilled in the art that various changes and modifications can be made herein without departing from the scope of the invention as defined by the appended claims.

What is claimed is:

1. A percutaneous surgical instrument comprising:
   an actuator assembly comprising:
   a proximal end;
   a distal end;
   a cable connector;
   a suction connector configured to connect to suction;
   a bolt;
   a horn mounted to the bolt;
   at least two piezoelectric ceramic rings disposed on the bolt between the horn and a back plate and configured to impart a vibration frequency to the horn;
   a probe set removably mounted to the horn at the distal end and comprising:
   at least one disturber configured to introduce a disturbance to the actuator assembly;
   a spring;
   an adjusting nut that is movable to adjust the spring force against the disturber thereby adjusting the disturbance of the at least one disturber; and
   a fixed probe;
   an operating switch; and
   a generator having a microprocessor and being connected to the actuator assembly through a cable and configured to power the at least two piezoelectric ceramic rings, wherein the microprocessor facilitates control of the vibration frequency and in response to the operating switch.

2. The percutaneous surgical instrument according to claim 1 wherein said fixed probe includes a lumen coupled with the suction connector and configured to impart suction to a surrounding environment.

3. The percutaneous surgical instrument according to claim 1 wherein said fixed probe comprises a wire.

4. The percutaneous surgical instrument according to claim 1 wherein the vibration frequency comprises one or more of a pulse cycle and a duty cycle.

5. The percutaneous surgical instrument according to claim 1 wherein the at least one disturber is formed of stainless steel.

6. The percutaneous surgical instrument according to claim 2 further comprising an actuator switch that facilitates selective imparting of suction to a surrounding environment through the lumen.

* * * * *

UNITED STATES PATENT AND TRADEMARK OFFICE
CERTIFICATE OF CORRECTION

| | |
|---|---|
| PATENT NO. | : 9,566,079 B2 |
| APPLICATION NO. | : 14/933234 |
| DATED | : February 14, 2017 |
| INVENTOR(S) | : Tao Song et al. |

It is certified that error appears in the above-identified patent and that said Letters Patent is hereby corrected as shown below:

In the Specification

Column 1, Line 12, delete "Field of the Invention";
Column 1, Line 35, change "object" to --objects--;
Column 1, Line 49, change "on 10 the" to --on the--;
Column 1, Lines 61-62, change "surgical 20 applications" to --surgical applications--;
Column 2, Line 15, change "above-described" to --above-described drawings--;
Column 2, Line 18, change "and 10 calculi" to --and calculi--; and
Column 2, Line 23, change "suction 15 connector 2" to --suction connector 2--.

Signed and Sealed this
Fourth Day of July, 2017

Joseph Matal
*Performing the Functions and Duties of the*
*Under Secretary of Commerce for Intellectual Property and*
*Director of the United States Patent and Trademark Office*